US010223785B2

(12) United States Patent
Kitamura et al.

(10) Patent No.: US 10,223,785 B2
(45) Date of Patent: Mar. 5, 2019

(54) IMAGE PROCESSING APPARATUS, IMAGE PROCESSING METHOD, AND COMPUTER-READABLE RECORDING MEDIUM EXTRACTING ONE OR MORE REPRESENTATIVE IMAGES

(71) Applicant: OLYMPUS CORPORATION, Tokyo (JP)

(72) Inventors: Makoto Kitamura, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 103 days.

(21) Appl. No.: 15/263,421

(22) Filed: Sep. 13, 2016

(65) Prior Publication Data

US 2016/0379363 A1 Dec. 29, 2016

Related U.S. Application Data

(63) Continuation of application No. PCT/JP2015/053133, filed on Feb. 4, 2015.

(30) Foreign Application Priority Data

Mar. 14, 2014 (JP) ................................ 2014-052613

(51) Int. Cl.
*G06K 9/00* (2006.01)
*G06T 7/00* (2017.01)
(Continued)

(52) U.S. Cl.
CPC .............. *G06T 7/0012* (2013.01); *A61B 1/00* (2013.01); *A61B 1/0005* (2013.01);
(Continued)

(58) Field of Classification Search
CPC ......... G06T 7/0012; G06T 2207/10068; G06T 2207/30092; G06T 2207/10016;
(Continued)

(56) References Cited

U.S. PATENT DOCUMENTS 7,088,850 B2 * 8/2006 Wei ....................... G06T 7/0012 382/128
7,756,309 B2 * 7/2010 Gholap ............ G06F 17/30247 382/128
(Continued)

FOREIGN PATENT DOCUMENTS

CN 102469925 A 5/2012
CN 105407787 A 3/2016
(Continued)

OTHER PUBLICATIONS

Chinese Office Action dated Jun. 28, 2017 in Chinese Patent Application No. 201580013805.2.
(Continued)

*Primary Examiner* — Li Liu
(74) *Attorney, Agent, or Firm* — Scully, Scott, Murphy & Presser, P.C.

(57) ABSTRACT

An image processing apparatus includes: a detection unit configured to detect images of interest including regions of interest that are estimated as an object to be detected, from a group of a series of images acquired by sequentially imaging a lumen of a living body; an image-of-interest group extracting unit configured to extract a group of images of interest including an identical region of interest, from the images of interest detected by the detection unit; and a representative image extracting unit configured to extract one or more representative images from the group of images
(Continued)

of interest, based on at least one of correlation of the regions of interest with the object to be detected, and visibility of the regions of interest.

21 Claims, 9 Drawing Sheets

(51) Int. Cl.

| | |
|---|---|
| ***G06F 17/30*** | (2006.01) |
| ***A61B 1/00*** | (2006.01) |
| ***A61B 1/04*** | (2006.01) |
| ***A61B 5/02*** | (2006.01) |
| ***G06K 9/46*** | (2006.01) |

(52) U.S. Cl.
CPC ............ *A61B 1/00009* (2013.01); *A61B 1/04* (2013.01); *A61B 1/041* (2013.01); *A61B 5/02042* (2013.01); *G06F 17/30799* (2013.01); *G06K 9/4652* (2013.01); *G06K 2209/05* (2013.01); *G06T 2207/10016* (2013.01); *G06T 2207/10024* (2013.01); *G06T 2207/10068* (2013.01); *G06T 2207/30092* (2013.01)

(58) Field of Classification Search
CPC ......... G06T 2207/10024; G06T 7/0016; G06T 7/11; G06T 7/174; G06T 7/32; G06T 7/33; G06K 2209/05; G06K 9/4652
See application file for complete search history.

(56) References Cited

U.S. PATENT DOCUMENTS

| | | | | |
|---|---|---|---|---|
| 8,014,576 | B2 * | 9/2011 | Collins .................... | A61B 8/08 382/128 |
| 9,186,051 | B2 | 11/2015 | Hirota | |
| 9,547,494 | B2 | 1/2017 | Matsuzaki | |
| 9,898,664 | B2 | 2/2018 | Matsuzaki | |
| 2007/0195165 | A1 | 8/2007 | Hirakawa | |
| 2008/0212881 | A1 | 9/2008 | Hirakawa | |
| 2009/0309961 | A1 | 12/2009 | Miyashita | |
| 2011/0069876 | A1 * | 3/2011 | Kanda ................ | A61B 1/00052 382/134 |
| 2012/0114203 | A1 | 5/2012 | Hirota | |
| 2014/0376792 | A1 | 12/2014 | Matsuzaki et al. | |
| 2016/0148053 | A1 | 5/2016 | Matsuzaki | |

FOREIGN PATENT DOCUMENTS

| | | | |
|---|---|---|---|
| JP | 2006-320650 | A | 11/2006 |
| JP | 2009-297365 | A | 12/2009 |
| JP | 2011-024727 | A | 2/2011 |
| JP | 2013-183912 | A | 9/2013 |
| WO | 2013/133370 | A1 | 9/2013 |

OTHER PUBLICATIONS

International Search Report dated Apr. 21, 2015 issued in PCT/JP2015/053133.

* cited by examiner

IMAGE PROCESSING APPARATUS, IMAGE PROCESSING METHOD, AND COMPUTER-READABLE RECORDING MEDIUM EXTRACTING ONE OR MORE REPRESENTATIVE IMAGES

CROSS REFERENCES TO RELATED APPLICATIONS

This application is a continuation of PCT international application Ser. No. PCT/JP2015/053133, filed on Feb. 4, 2015 which designates the United States, incorporated herein by reference, and which claims the benefit of priority from Japanese Patent Application No. 2014-052613, filed on Mar. 14, 2014, incorporated herein by reference.

BACKGROUND

1. Technical Field

The disclosure relates to an image processing apparatus, an image processing method, and a computer-readable recording medium, for extracting a representative image from an image group obtained by imaging a lumen of a living body.

2. Related Art

A technique has been known in which a group of a series of images (hereinafter, also referred to as intraluminal image group) is obtained by imaging a lumen of a living body in chronological order using a medical observation apparatus such as an endoscope or a capsule endoscope, and an image showing a region of interest such as an abnormal region is extracted as a representative image from the group of a series of images. A user can observe the representative image extracted from the image group, so that a burden during detailed observation of a large number of images is reduced, and diagnosis is made accurately and efficiently.

For example, JP 2011-24727 A discloses an image processing apparatus in which regions of interest are detected from an intraluminal image group obtained in chronological order, the detected regions of interest are classified, based on the features thereof, into identical groups of regions of interest being chronologically adjacent and having similar features, a representative region of each group is selected from the regions of interest classified in the each group, based on an average value of the features and an image including the selected representative region is output as a representative image.

SUMMARY

In some embodiments, an image processing apparatus includes: a detection unit configured to detect images of interest including regions of interest that are estimated as an object to be detected, from a group of a series of images acquired by sequentially imaging a lumen of a living body; an image-of-interest group extracting unit configured to extract a group of images of interest including an identical region of interest, from the images of interest detected by the detection unit; and a representative image extracting unit configured to extract one or more representative images from the group of images of interest, based on at least one of correlation of the regions of interest with the object to be detected, and visibility of the regions of interest.

In some embodiments, an image processing method causes a calculation unit of a computer to perform image processing based on image data of a group of a series of images which are acquired by sequentially imaging a lumen of a living body and recorded in a recording unit. The method includes: a detection step of detecting images of interest including regions of interest that are estimated as an object to be detected, from the group of a series of images; an image-of-interest group extracting step of extracting a group of images of interest including an identical region of interest, from the images of interest detected in the detection step; and a representative image extracting step of extracting one or more representative images from the group of images of interest, based on at least one of correlation of the regions of interest with the object to be detected, and visibility of the regions of interest.

In some embodiments, a non-transitory computer-readable recording medium with an executable program stored thereon is provided. The program causes a computer to execute: a detection step of detecting images of interest including regions of interest that are estimated as an object to be detected, from a group of a series of images acquired by sequentially imaging a lumen of a living body; an image-of-interest group extracting step of extracting a group of images of interest including an identical region of interest, from the images of interest detected in the detection step; and a representative image extracting step of extracting one or more representative images from the group of images of interest, based on at least one of correlation of the regions of interest with the object to be detected, and visibility of the regions of interest.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an image processing apparatus, an image processing method, and an image processing program according to embodiments of the present invention will be described with reference to the drawings. Note that the present invention is not limited to these embodiments. The same reference signs are used to designate the same elements throughout the drawings.

First Embodiment

Figure 1:
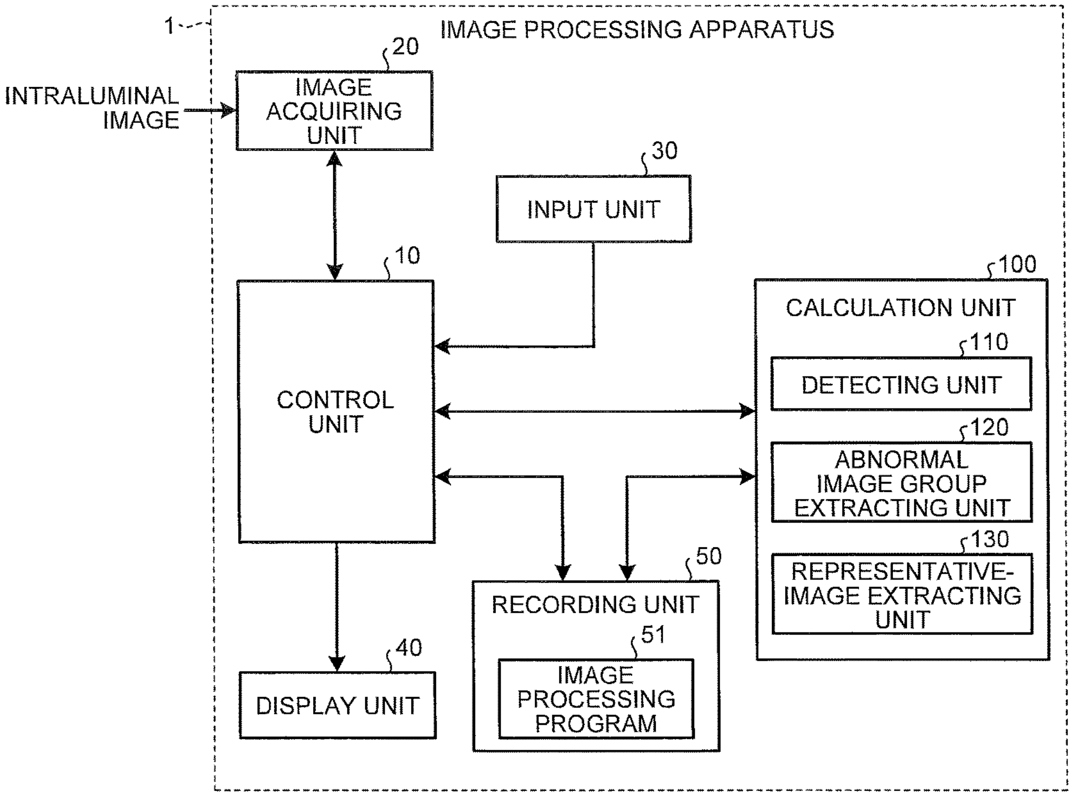
FIG. 1 is a block diagram illustrating a configuration of an image processing apparatus according to a first embodiment of the present invention.

FIG. 1 is a block diagram illustrating an image processing apparatus according to a first embodiment of the present invention. The image processing apparatus 1 according to the first embodiment is an apparatus detecting an image (image of interest) group having images including a region of interest being a region seeming to be an object to be detected in diagnosis, from a group of a series of images acquired by sequentially imaging a lumen of a living body as a subject by a medical observation apparatus such as a capsule endoscope, and extracting a representative image from the detected image-of-interest group. An image indicating the lumen of the living body (also referred to as intraluminal image) is normally a color image having a pixel level (pixel value) corresponding to wavelength components of R (red), G (green), and B (blue) at each pixel position. In the following description, abnormal regions such as bleeding, redness, aphtha, and ulcer are detected as the region of interest, and a representative image is extracted from an image (abnormal image) group having images including the abnormal regions, but the region of interest is not limited to the above-exemplified abnormal regions.

As illustrated in FIG. 1, the image processing apparatus 1 includes a control unit 10 for controlling the operation of the image processing apparatus 1 as a whole, an image acquiring unit 20 for acquiring image data corresponding to an intraluminal image captured by the medical observation apparatus such as a capsule endoscope, an input unit 30 for inputting a signal to the control unit 10, according to operation from outside, a display unit 40 for displaying various information or images, a recording unit 50 for storing the image data acquired by the image acquiring unit 20 or various programs, and a calculation unit 100 for performing predetermined image processing on the image data.

The control unit 10 includes hardware such as a CPU. The control unit 10 reads the various programs recorded in the recording unit 50 to perform transfer of commands or data to each unit of the image processing apparatus 1 according to image data input from the image acquiring unit 20 or a signal input from the input unit 30, and performs overall control of the image processing apparatus 1.

The image acquiring unit 20 is appropriately configured depending on modes of a system having a capsule endoscope for imaging an inside of the subject. For example, if a portable recording medium is used to transmit and receive image data to and from the capsule endoscope, the image acquiring unit 20 includes a reader device removably mounting the recording medium to read image data of recorded images. In addition, when a server is provided to save image data of images captured by the capsule endoscope, the image acquiring unit 20 includes a communication device or the like connected to the server, and performs data communication with the server to acquire the image data.

The input unit 30 includes, for example, an input device such as a keyboard, a mouse, a touch panel, or various switches, and outputs, to the control unit 10, an input signal generated according to the operation from outside to the input device.

The display unit 40 includes a display device such as an LCD or an EL display, and displays various screens including the intraluminal image under control of the control unit 10.

The recording unit 50 includes various IC memories including a RAM and a ROM such as a updatable flash memory, a hard disk incorporated or connected with a data communication terminal, or an information recording device such as a CD-ROM and a reader or the like therefor. The recording unit 50 stores the programs for operating the image processing apparatus 1 and causing the image processing apparatus 1 to perform various functions, data used during execution of the programs, or the like, in addition to the image data of the intraluminal image acquired by the image acquiring unit 20. Specifically, the recording unit 50 stores an image processing program 51, determination criteria used for detecting abnormal regions, determination criteria used for extracting a representative image, and the like. The image processing program 51 causes the image processing apparatus 1 to perform image processing for detecting the abnormal regions such as bleeding, redness, aphtha, ulcer, and the like from the intraluminal images, extracting abnormal image groups each including identical abnormal regions from images (abnormal images) including these abnormal regions, and extracting a representative image from each of the abnormal image groups.

The calculation unit 100 includes hardware such as a CPU, reads the image processing program 51 to perform image processing for extracting abnormal image groups each including an identical abnormal region from the intraluminal images, and extracting a representative image from each abnormal image group.

Next, a configuration of the calculation unit 100 will be described. As illustrated in FIG. 1, the calculation unit 100 includes a detecting unit 110 for detecting abnormal images including abnormal regions from a group of a series of images, an abnormal image group extracting unit 120 for extracting abnormal image groups each including identical abnormal regions from the abnormal images detected by the detecting unit 110, and a representative-image extracting unit 130 for extracting a representative image from the extracted abnormal image groups based on at least any one of a degree of importance and visibility of each abnormal region. Here, the degree of importance of the abnormal region represents correlation between an object to be detected and each abnormal region in intraluminal image diagnosis, in other words, likelihood of the object to be detected, and the stronger the correlation (increased likelihood of the object to be detected), the higher the degree of importance. For example, when a bleeding source is the object to be detected, it is determined that the higher the likelihood that a detected abnormal region is the bleeding source, the higher the degree of importance of the abnormal region.

The detecting unit 110 detects an abnormal region based on various features of the intraluminal image. In the first embodiment, description will be made of an example of detecting the abnormal region based on color features (color information) of the intraluminal image. Here, an abnormal region such as bleeding, redness, or vascular abnormality is indicated by a specific reddish color, and an abnormal region such as ulcer or aphtha is indicated by a specific whitish color. The detecting unit 110 uses color features, for example, color components (R component, G component, B component) of the pixel value, or values secondarily calculated by a known conversion from the color components (e.g., color difference calculated by YCbCr conversion, hue and saturation calculated by HSI conversion, color ratio such as G/R or B/G) to detect a region indicated by any of the specific colors in the intraluminal image, and defines the region as the abnormal region. More specifically, the detecting unit 110 develops determination criteria (color range) for abnormal regions in advance, based on color features of various abnormal regions having been collected, and records the determination criteria in the recording unit 50. When an abnormal region is detected from the intraluminal image, the determination criteria are read from the recording unit 50, color features are calculated for each pixel constituting the intraluminal image, the color features of each pixel are compared with the determination criteria, and the abnormal region is detected from the intraluminal image.

Note that detection of an abnormal region is not limited to the above-mentioned method, and various known methods can be applied as long as the abnormal region can be detected. For example, a method based on a feature space distance with a representative color feature may be used. Further, in the above description, the color features of a pixel constituting the intraluminal image is used to detect the abnormal region, but the intraluminal image may be divided into small regions based on edge information or the like in the image so that color features of a small region is used to detect the abnormal region. Still further, the abnormal region may be detected using shape features or texture features other than the color features.

The abnormal image group extracting unit 120 is an image-of-interest group extracting unit which extracts, as one abnormal image group, images including identical abnormal regions from the abnormal regions detected by the detecting unit 110. More specifically, the abnormal image group extracting unit 120 extracts, as an abnormal image group including identical abnormal regions, continuous time-series abnormal images from the abnormal images including abnormal regions.

Note that, for extraction of the abnormal image groups each including identical abnormal regions, various known methods can be applied, in addition to the above described extraction method. For example, a change between images may be determined based on normalized cross correlation between abnormal images, a change in motion vector, or a change in pixel value (luminance value or G component value) so that an abnormal image group having a change not more than a predetermined value is extracted as the abnormal image group including identical abnormal regions. Alternatively, a difference value in shape feature (area, circularity, or the like) or color feature (color ratio, hue, or the like) of an abnormal region may be calculated between abnormal images so that an abnormal image group having the difference value not more than a predetermined value is extracted as the abnormal image group including identical abnormal regions.

The representative-image extracting unit 130 extracts, as the representative image, an abnormal image including an abnormal region having a high degree of importance or an abnormal image having good visibility of the abnormal region, from each of the abnormal image groups each including identical abnormal regions.

Figure 2:
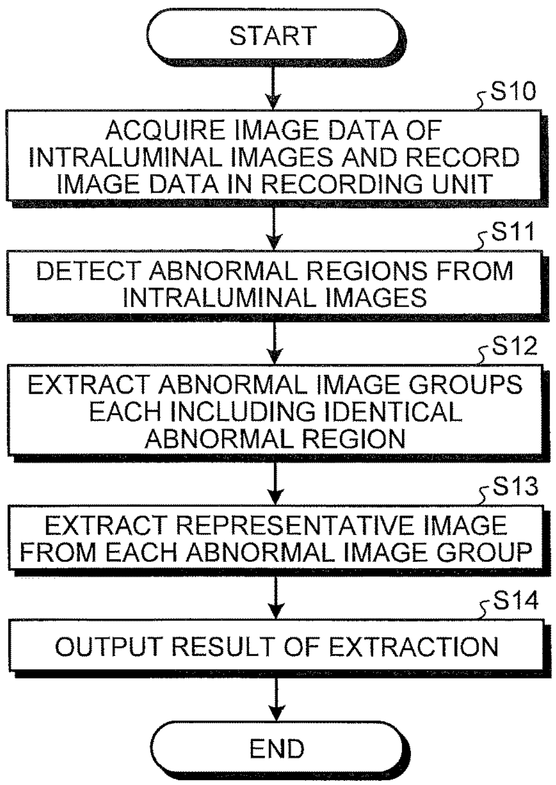
FIG. 2 is a flowchart illustrating operation of the image processing apparatus illustrated in FIG. 1.

Next, operation of the image processing apparatus 1 illustrated in FIG. 1 will be described. FIG. 2 is a flowchart illustrating the operation of the image processing apparatus 1. First, in step S10, the image processing apparatus 1 acquires image data of a series of intraluminal images captured in chronological order through the image acquiring unit 20, and records the image data in the recording unit 50.

In the following step S11, the detecting unit 110 sequentially reads the image data of the intraluminal images recorded in the recording unit 50 to perform a process of detecting abnormal regions from the intraluminal images. Specifically, the detecting unit 110 reads the determination criteria for abnormal regions previously recorded in the recording unit 50, compares each of the color features of the pixels constituting the intraluminal images, with this determination criteria, and determines the abnormal regions.

Figure 3:
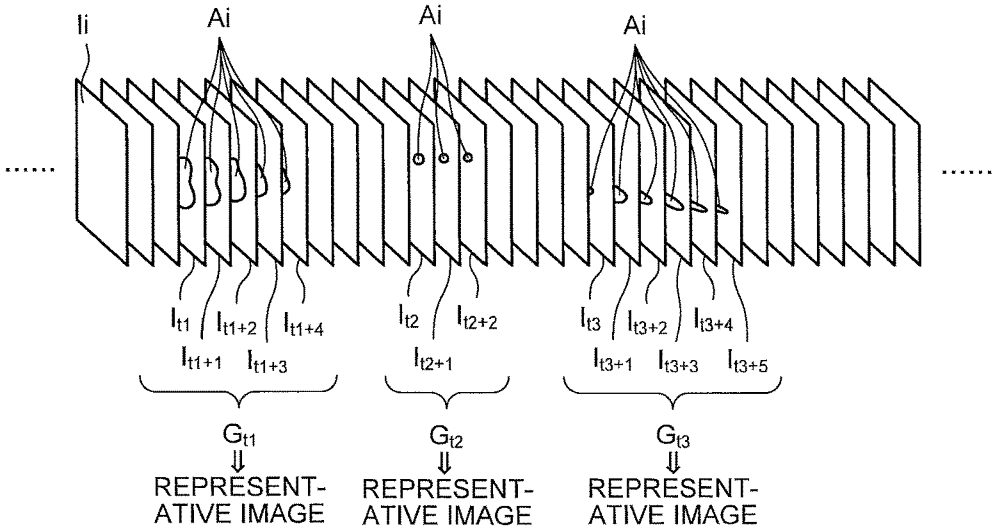
FIG. 3 is a schematic diagram illustrating a series of intraluminal images acquired in chronological order.

FIG. 3 is a schematic diagram illustrating the series of intraluminal images acquired in chronological order. Here, a subscript i (i=1, 2, . . . ) of an intraluminal image $I_i$ represents an arrangement sequence (imaging sequence) of the intraluminal images. In the processing in step S11, abnormal images (intraluminal images $I_i$, where i=t1 to t1+4, t2 to t2+2, t3 to t3+5) including abnormal regions $A_i$ are detected from these intraluminal images $I_i$. Hereinafter, the intraluminal image $I_i$ extracted as the abnormal image is also referred to as abnormal image $I_i$.

In the following step S12, the abnormal image group extracting unit 120 extracts abnormal image groups each including an identical abnormal region, from the abnormal images detected in step S11. Specifically, continuous time-series abnormal images are extracted as the abnormal image groups each including the identical abnormal region. Therefore, for example as illustrated in FIG. 3, an abnormal image group $G_{t1}$ including abnormal images $I_{t1}$ to $I_{t1+4}$, an abnormal image group $G_{t2}$ including abnormal images $I_{t2}$ to $I_{t2+2}$, and an abnormal image group $G_{t3}$ including abnormal images $I_{t3}$ to $I_{t3+t5}$ are extracted as identical abnormal regions, respectively.

In the following step S13, the representative-image extracting unit 130 extracts, as the representative image, at least one abnormal image having a high degree of importance of the abnormal region, or abnormal image having good visibility of the abnormal region, from each of the abnormal image groups extracted in step S12. The number of representative images to be extracted may have a constant value (e.g., one from each abnormal image group), or may be determined according to the number of abnormal images belonging to an abnormal image group (e.g., α times the number of abnormal images, where $0<\alpha<1$). If the number of representative images is determined according to the number of abnormal images and if the number of representative images is less than one, at least one representative image is extracted. Alternatively, all abnormal images satisfying a predetermined criterion (e.g., abnormal images having a color feature not less than a predetermined threshold) may be extracted as the representative image, without specifying the number of representative images to be extracted.

A method for extracting a representative image is not particularly limited. For example, the first image of each abnormal image group may be extracted as the representative image. Alternatively, the representative image may be extracted based on the color features of the identical abnormal region in each abnormal image group. Specifically, when an abnormal region is indicated by the specific reddish color, an abnormal image having a stronger red color in the abnormal region is preferentially extracted as the representative image, and when an abnormal region is indicated by the specific whitish color, an abnormal image having a stronger white color in the abnormal region is preferentially extracted as the representative image. Furthermore, an abnormal image having an abnormal region larger in size, or an abnormal image having an abnormal region positioned near the center may be preferentially extracted as the representative image.

In the following step S14, the calculation unit 100 outputs information indicating the representative image extracted from each abnormal image group in step S13. Accordingly, the recording unit 50 adds information (flag) indicating the representative image to image data of an intraluminal image extracted as the representative image.

As described above, according to the first embodiment of the present invention, abnormal images extracted from the intraluminal images are divided into abnormal image groups each including identical abnormal regions, representative images are extracted from the abnormal image groups, based on the degree of importance or visibility of the abnormal regions, and an intraluminal image beneficial to diagnosis can be preferentially extracted as the representative image. Furthermore, at this time, at least one representative image is extracted from each abnormal image group, so that all abnormal images are extracted, and the number of representative images can be reduced while preventing failure to extract the abnormal image to be observed by a user. Accordingly, detailed observation of the representative images thus extracted allows the user to make accurate and efficient diagnosis.

Modification 1-1

Next, modification 1-1 of the first embodiment of the present invention will be described.

In step S13, the representative-image extracting unit 130 may calculate intensities of reddish color of the abnormal regions to extract a representative image based on the intensities of reddish color. For example, when identical abnormal regions in an abnormal image group have bleeding, redness, or vascular abnormality, it can be said that an abnormal image having stronger reddish color in the abnormal region has a higher degree of importance. The intensity of reddish color is indicated by the color ratio G/R, and the smaller the color ratio G/R, the stronger the reddish color.

Specifically, first, the representative-image extracting unit 130 calculates an average value of the color ratios G/R in pixels constituting the abnormal region, for each abnormal image belonging to an abnormal image group to be processed. Then, a predetermined number of abnormal images are extracted as the representative images, in ascending order of average values of the color ratios G/R. Here, this method uses the color ratio G/R, but hue H or the like of HSI may be similarly used.

Modification 1-2

Next, modification 1-2 of the first embodiment of the present invention will be described.

In step S13, the representative-image extracting unit 130 may calculate intensities of white color of the abnormal regions to extract a representative image based on the intensities of white color. For example, when identical abnormal regions in an abnormal image group have aphtha or ulcer, it can be said that an abnormal image having a stronger white color in the abnormal region has a higher degree of importance. The intensity of white color is indicated by the color ratios G/R and B/G, and the larger the color ratios G/R and B/G, the stronger the whitish color.

Specifically, first, the representative-image extracting unit 130 calculates average values of the color ratios G/R and B/G in pixels constituting the abnormal region, for each abnormal image belonging to an abnormal image group to be processed. Then, a predetermined number of abnormal images are extracted as the representative images, in descending order of total values of the average value of the color ratios G/R and the average value of the color ratios B/G. Here, this method uses the color ratios G/R and B/G, but hue H, saturation S, or the like of HSI may be similarly used.

Modification 1-3

Next, modification 1-3 of the first embodiment of the present invention will be described.

In step S13, the representative-image extracting unit 130 may detect, from an abnormal image, a region (hereinafter, referred to as unnecessary region), such as noise, bubble, or residue, having little or no correlation with the abnormal region being the object to be detected, to extract a representative image based on the unnecessary region. It can be said that an abnormal image having a smaller unnecessary region has higher visibility.

Specifically, first, the representative-image extracting unit 130 detects the unnecessary region such as noise, bubble, or residue, for each abnormal image belonging to an abnormal image group to be processed. For detection of the unnecessary region, various known methods can be applied. For example, feature distribution of color features (values of R component, G component, and B component of a pixel value, values secondarily calculated by known conversion of the values of the color components (color difference calculated by YCbCr conversion, hue or saturation calculated by HSI conversion, color ratio such as G/R or B/G, or the like)), shape features (shape information such as histograms of oriented gradients (HOG), areas, circumferential length, or Feret's diameter), or texture features (local binary pattern (LBP), simultaneous normal matrix, or the like) is previously calculated, for noise, bubble, residue, and mucosal regions shown in an intraluminal image. Then, based on the feature distribution, determination criteria are developed by a learning tool such as a support vector machine (SVM). Features calculated for each abnormal image are compared with the determination criteria, and the unnecessary region such as noise, bubble, or residue can be detected.

Next, the representative-image extracting unit 130 calculates the total area (total pixels) of the detected unnecessary regions, for each abnormal image. Then, a predetermined number of abnormal images are extracted as the representative images, in ascending order of total areas.

Modification 1-4

Next, modification 1-4 of the first embodiment of the present invention will be described.

In step S13, the representative-image extracting unit 130 may calculate brightness of the abnormal regions to extract a representative image based on the brightness. It can be said that an abnormal image having higher brightness has higher visibility.

Specifically, first, the representative-image extracting unit 130 calculates an average value (average luminance value) of the G component in pixels constituting an abnormal region, for each abnormal image belonging to an abnormal image group to be processed. Then, a predetermined number of abnormal images are extracted as the representative images, in descending order of average luminance values.

Modification 1-5

Next, modification 1-5 of the first embodiment of the present invention will be described.

In step S13, the representative-image extracting unit 130 may calculate contrasts of the abnormal regions to extract a representative image based on the contrast. It can be said that an abnormal image having a higher contrast has higher visibility.

Specifically, first, the representative-image extracting unit 130 calculates an absolute value of a difference between an average value (average luminance value) of the G components in pixels constituting an abnormal region, and an average value (average luminance value) of the G components in pixels constituting regions other than the abnormal region, for each abnormal image belonging to an abnormal image group to be processed. Then, a predetermined number of abnormal images are extracted as the representative images, in descending order of absolute values of the difference.

Modification 1-6

Next, modification 1-6 of the first embodiment of the present invention will be described.

In step S13, the representative-image extracting unit 130 may calculate sizes of the abnormal regions to extract a representative image based on the sizes. It can be said that an abnormal image having a larger abnormal region has higher visibility.

Specifically, first, the representative-image extracting unit 130 calculates a total area (total pixels) of an abnormal region, for each abnormal image belonging to an abnormal image group to be processed. Then, a predetermined number of abnormal images are extracted as the representative images, in descending order of total areas of the abnormal regions.

Modification 1-7

Next, modification 1-7 of the first embodiment of the present invention will be described.

In step S13, the representative-image extracting unit 130 may count the number of the abnormal regions in the abnormal images to extract a representative image based on the counted number. It can be said that an abnormal image having a larger number of abnormal regions has higher visibility.

Specifically, first, the representative-image extracting unit 130 counts the number of abnormal regions, for each abnormal image belonging to an abnormal image group to be processed. Then, a predetermined number of abnormal images are extracted as the representative images, in descending order of the number of abnormal regions.

Modification 1-8

Next, modification 1-8 of the first embodiment of the present invention will be described.

In step S13, the representative-image extracting unit 130 may extract a representative image based on the positions of the abnormal regions in the abnormal images. It can be said that an abnormal image having an abnormal region positioned near the center of the image has higher visibility.

Specifically, first, the representative-image extracting unit 130 calculates a distance between each of four sides of an image and a centroid of the abnormal region, for each abnormal image belonging to an abnormal image group to be processed, and then defines a value of the shortest distance as a distance from an end of the image to the abnormal region. It can be said that an image having a longer distance has an abnormal region located near the center of the image. Then, the representative-image extracting unit 130 extracts a predetermined number of abnormal images as the representative images, in descending order of distances from an end of the image.

Note that, as the distance from an end of the image to the abnormal region, distances between four sides of the image and positions of a boundary of the abnormal region nearest to the four sides may be calculated to adopt a value of the shortest distance. Alternatively, distances between the center positions of abnormal images and the centroids of abnormal regions may be calculated to extract abnormal images as the representative images in ascending order of distances.

Such representative image extraction methods as described in modifications 1-1 to 1-8 may be adapted singularly or in any combination of differently weighted extraction methods thereof.

Second Embodiment

Next, a second embodiment of the present invention will be described.

Figure 4:
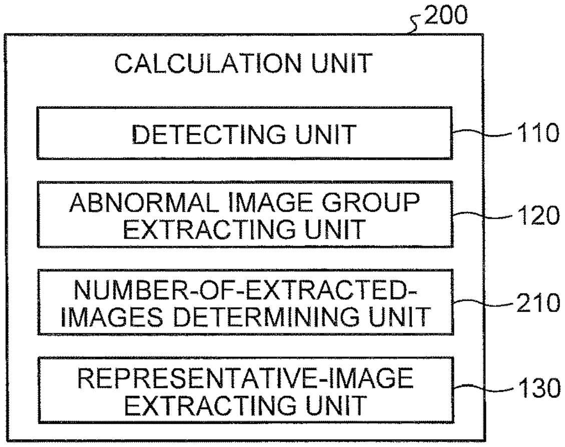
FIG. 4 is a block diagram illustrating a configuration of a calculation unit of an image processing apparatus according to a second embodiment of the present invention.

FIG. 4 is a block diagram illustrating a configuration of a calculation unit of an image processing apparatus according to a second embodiment of the present invention. As illustrated in FIG. 4, the image processing apparatus according to the second embodiment includes a calculation unit 200 illustrated in FIG. 4, instead of the calculation unit 100 illustrated in FIG. 1. Configurations and operations of units other than the calculation unit 200 are similar to those of the first embodiment.

The calculation unit 200 further includes a number-of-extracted-images determining unit 210, in addition to the detecting unit 110, the abnormal image group extracting unit 120, and the representative-image extracting unit 130. The number-of-extracted-images determining unit 210 adaptively determines the number of representative images to be extracted, based on at least any one of degree of importance and visibility of the abnormal region in each abnormal image group extracted by the abnormal image group extracting unit 120. Note that, operations of the detecting unit 110, the abnormal image group extracting unit 120, and the representative-image extracting unit 130 are similar to those of the first embodiment.

Figure 5:
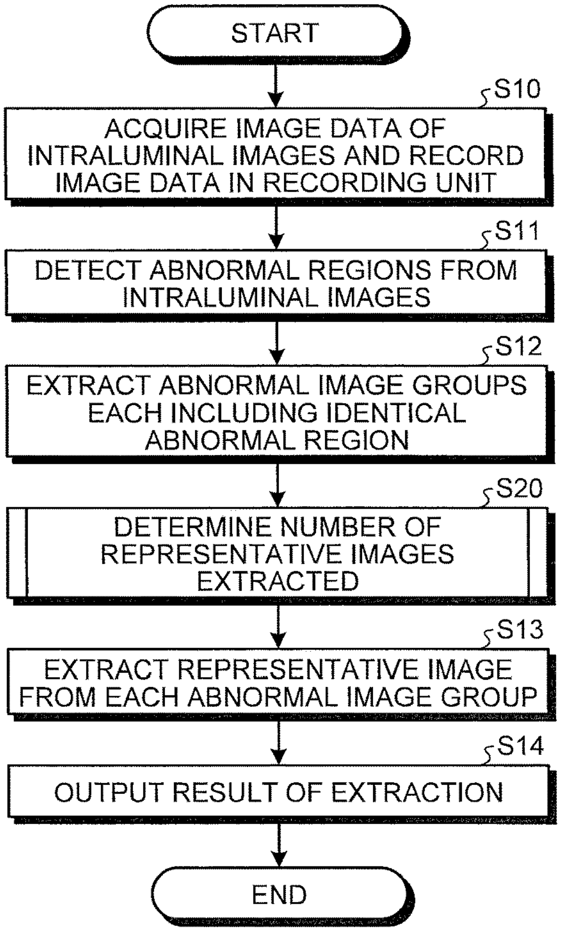
FIG. 5 is a flowchart illustrating operation of the image processing apparatus according to the second embodiment.

Next, operation of the image processing apparatus according to the second embodiment of the present invention will be described. FIG. 5 is a flowchart illustrating operation of the image processing apparatus according to the second embodiment. Note that, steps S10 to S12 illustrated in FIG. 5 are similar to those of the first embodiment (see FIG. 2).

In step S20 subsequent to step S12, the number-of-extracted-images determining unit 210 determines the number of representative images to be extracted, for each of the abnormal image groups extracted in step S12. At this time, in order to prevent missing an abnormal image group including an abnormal region having a high degree of importance, the number-of-extracted-images determining unit 210 determines the number of representative images to be extracted, based on the degree of importance of the abnormal region, so that a larger number of representative images are extracted.

Figure 6:
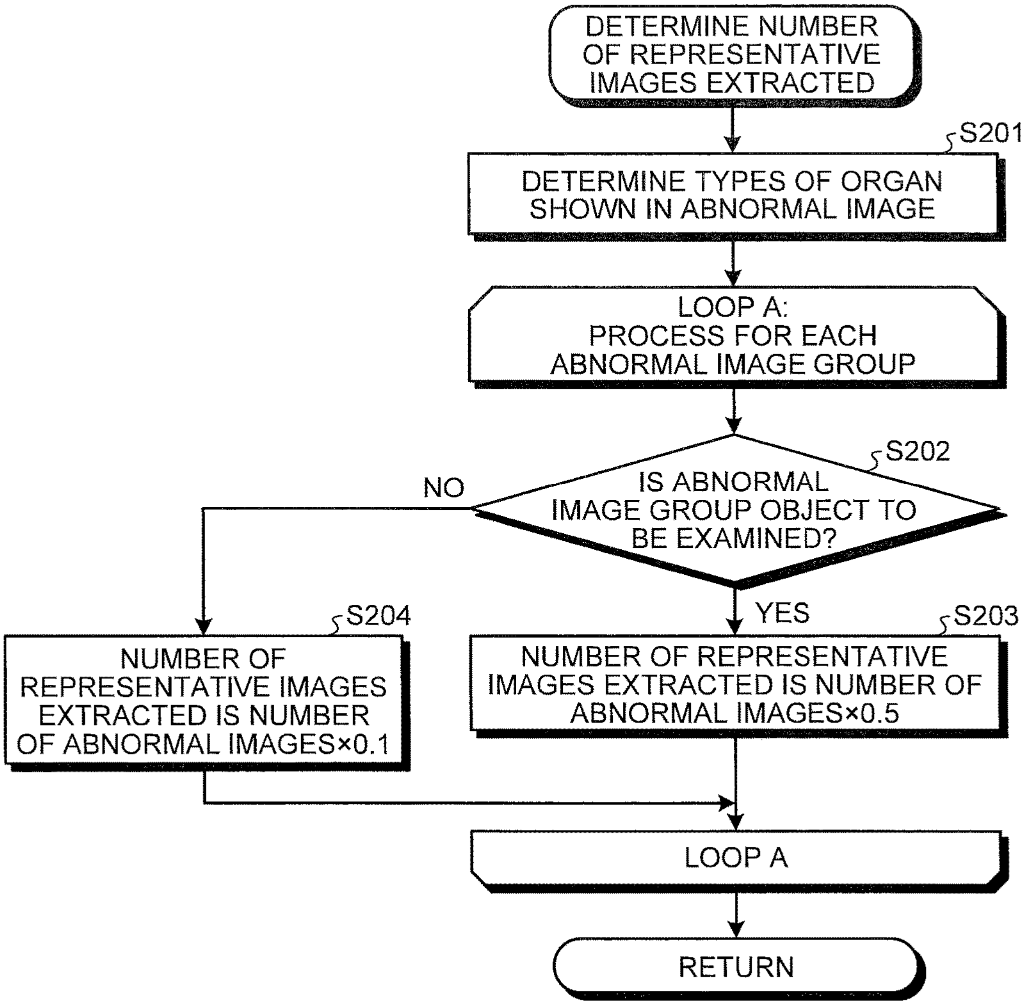
FIG. 6 is a flowchart illustrating a process of determining the number of representative images to be extracted, which is performed by a number-of-extracted-images determining unit illustrated in FIG. 4.

FIG. 6 is a flowchart illustrating a process of determining the number of representative images to be extracted, which is performed by the number-of-extracted-images determining unit 210. An example of determining the number of representative images to be extracted based on the types of organ as the degree of importance of the abnormal region, shown in each intraluminal image will be described below with reference to FIG. 6.

First, in step S201, the number-of-extracted-images determining unit 210 determines the types of organ shown in each abnormal image extracted from a series of intraluminal images. For determination of the types of organ, various known methods can be applied. A determination method disclosed in JP 2006-288612 A will be described below as an example.

First, a numerical range of each of color components (color elements) R, G, and B in an image showing each organ (esophagus, stomach, small intestine, or large intestine) in a lumen is previously determined. Then, respective average values of R components, G components, and B components of pixels in an abnormal image are calculated, and the average values are compared with the previously determined numerical ranges of the color components of the organs. Thus, when the average values of the color components calculated for the abnormal image are within the previously determined numerical ranges of the color components of the esophagus, an organ shown in the abnormal image is determined as esophagus. Similarly, when average values of the color components calculated for the abnormal image are within the previously determined numerical ranges of the color components of the stomach, an organ shown in the abnormal image is determined as stomach, when within the numerical ranges of the color components of the small intestine, an organ shown in the abnormal image is determined as small intestine, and when within the numerical ranges of the color components of the large intestine, an organ shown in the abnormal image is determined as large intestine.

Next, the number-of-extracted-images determining unit 210 performs processing of a loop A for each abnormal image group.

In step S202, the number-of-extracted-images determining unit 210 determines whether an abnormal image group to be processed is an object to be examined, based on a preset organ to be examined. Specifically, when more than half of abnormal images of the abnormal image group show the organ to be examined, the abnormal image group is determined to be the object to be examined, and when less than half of abnormal images show the organ to be examined, the abnormal image group is determined not to be the object to be examined.

When the abnormal image group is the object to be examined (step S202: Yes), the number-of-extracted-images determining unit 210 determines the number of representative images to be extracted, to be 0.5 times the number of abnormal images belonging to the abnormal image group (step S203). In contrast, when the abnormal image group is not the object to be examined (step S202: No), the number-of-extracted-images determining unit 210 determines the number of representative images to be extracted, to be 0.1 times the number of abnormal images belonging to the abnormal image group (step S204). Here, if the number of representative images to be extracted is not more than one after calculation in step S203 or step S204, the number of representative images to be extracted is determined to be one.

After completion of the loop A for all of the abnormal image groups extracted from the series of intraluminal images, the process returns to a main routine.

Processing in steps S13 and S14 subsequent to step S20 are similar to that of the first embodiment. At this time, in step S13, the representative-image extracting unit 130 extracts, from each abnormal image group, representative images by the number of representative images to be extracted, determined in step S20. For example, when the organ to be examined is small intestine, representative images are extracted from an abnormal image group in which more than half of abnormal images show the small intestine so that the number of representative images is 0.5 times the number of abnormal images. In contrast, from an abnormal image group in which more than half of abnormal images show esophagus, stomach, or large intestine, representative images are extracted so that the number of representative images is 0.1 times the number of abnormal images.

As described above, according to the second embodiment of the present invention, the number of representative images to be extracted from each abnormal image group is determined according to the degree of importance of the abnormal region, so that a larger number of representative images can be extracted from an abnormal image group including the abnormal region having a high degree of importance. Accordingly, the user can prevent missing the abnormal region having a high degree of importance, to make accurate and efficient diagnosis.

Modification 2-1

Next, modification 2-1 of the second embodiment of the present invention will be described.

In the above second embodiment, at least one representative image is extracted from each abnormal image group, but since an image showing an organ other than the object to be examined is considered to have low degree of importance, the representative image does not need to be extracted from an abnormal image group not being the object to be examined.

Specifically, in step S202 illustrated in FIG. 6, when an abnormal image group is the object to be examined (step S202: Yes), the number of representative images to be extracted is determined to be 0.5 times the number of abnormal images belonging to the abnormal image group, similarly to the second embodiment (step S203). Note that, at this time, if the number of representative images to be extracted is not more than one, the number of representative images to be extracted is determined to be one. In contrast, if the abnormal image group is not the object to be examined (step S202: No), the number of representative images to be extracted is determined to be 0 times the number of abnormal images belonging to the abnormal image group.

In this configuration, in step S13 (see FIG. 5) subsequent to step S20, for example, when the organ to be examined is small intestine, representative images are extracted from an abnormal image group in which more than half of abnormal images show the small intestine so that the number of representative images is 0.5 times the number of abnormal images. In contrast, from an abnormal image group in which more than half of abnormal images show esophagus, stomach, or large intestine, the representative images is not extracted.

As described above, according to modification 2-1, the representative image is only extracted from an abnormal image to be examined, and thus, the user can make efficient diagnosis.

Note that, coefficients (0.5 times, 0.1 times, and the like) for determining the number of representative images to be extracted according to the types of organ are not limited to the above description, and are appropriately set according to organs to be examined or the purpose of examination.

Modification 2-2

Next, modification 2-2 of the second embodiment of the present invention will be described.

In the second embodiment, the types of organ shown in the abnormal image is automatically determined by image processing, but the user may determine the types of organ.

Specifically, through image processing in the calculation unit 200, average colors of a series of intraluminal images are calculated, and a color bar having arrangement of the average colors in order of arrangement of intraluminal images (time-series order) is formed to be displayed on the display unit 40. A color difference (boundary) between average colors on this color bar corresponds to a boundary between organs in the series of intraluminal images. When a signal for selecting a specific point on the color bar is input from the input unit 30 to the control unit 10, according to the user's operation to the input unit 30, the control unit 10 inputs, to the calculation unit 200, an image number of an intraluminal image corresponding to the selected point. The calculation unit 200 identifies the types of organ shown in each intraluminal image, with an intraluminal image corresponding to the input image number as a boundary of organ.

Modification 2-3

Next, modification 2-3 of the second embodiment of the present invention will be described.

After acquisition of the image data in step S10, the calculation unit 200 may perform a process of determining the types of organ for the whole of the series of intraluminal images. Note that, the determination of the types of organ may be performed automatically similarly to the second embodiment, or may be performed manually by the user, similarly to modification 2-2.

In this configuration, the calculation unit 200 performs processing of steps S11, S12, and S20 illustrated in FIG. 5 on intraluminal images showing an organ to be examined (e.g., small intestine). In step S20, since the organ has been determined, the number of representative images to be extracted is merely determined according to the number of abnormal images belonging to each abnormal image group (e.g., 0.5 times the number of abnormal images belonging to the abnormal image group). The following steps S13 and S14 are similar to those of the second embodiment.

In contrast, the calculation unit 200 detects an abnormal region to extract an abnormal image from intraluminal images showing an organ other than the object to be examined (e.g., esophagus, stomach, or large intestine), subsequently extracts a predetermined number (e.g., small number such as ten) of abnormal images, for example, in descending order of intensity of reddish color of the abnormal region, or in descending order of intensity of white color of the abnormal region, and then outputs the abnormal images as the representative images. Note that, the intensity of reddish color is indicated by the color ratio G/R, and the smaller the color ratio G/R, the stronger the reddish color. Furthermore, the intensity of white color is indicated by the color ratios G/R and B/G, and the larger the color ratios G/R and B/G, the stronger the whitish color. Alternatively, the calculation unit 200 may detect a predetermined number (e.g., small number such as ten) of intraluminal images as the representative images, based on the color features (color ratio or the like described above) of the intraluminal images without detecting an abnormal region for the intraluminal images showing an organ other than the object to be examined. Furthermore, the representative image does not need to be extracted from the intraluminal images showing an organ other than the object to be examined.

Modification 2-4

Next, modification 2-4 of the second embodiment of the present invention will be described.

In step S20 illustrated in FIG. 5, the number-of-extracted-images determining unit 210 may adaptively determine the number of representative images to be extracted, based on the degree of importance of the abnormal image, other than the types of organ. A method for determining the number of representative images to be extracted based on the kinds of abnormal region will be described below, as an example of the degree of importance of the abnormal image.

Figure 7:
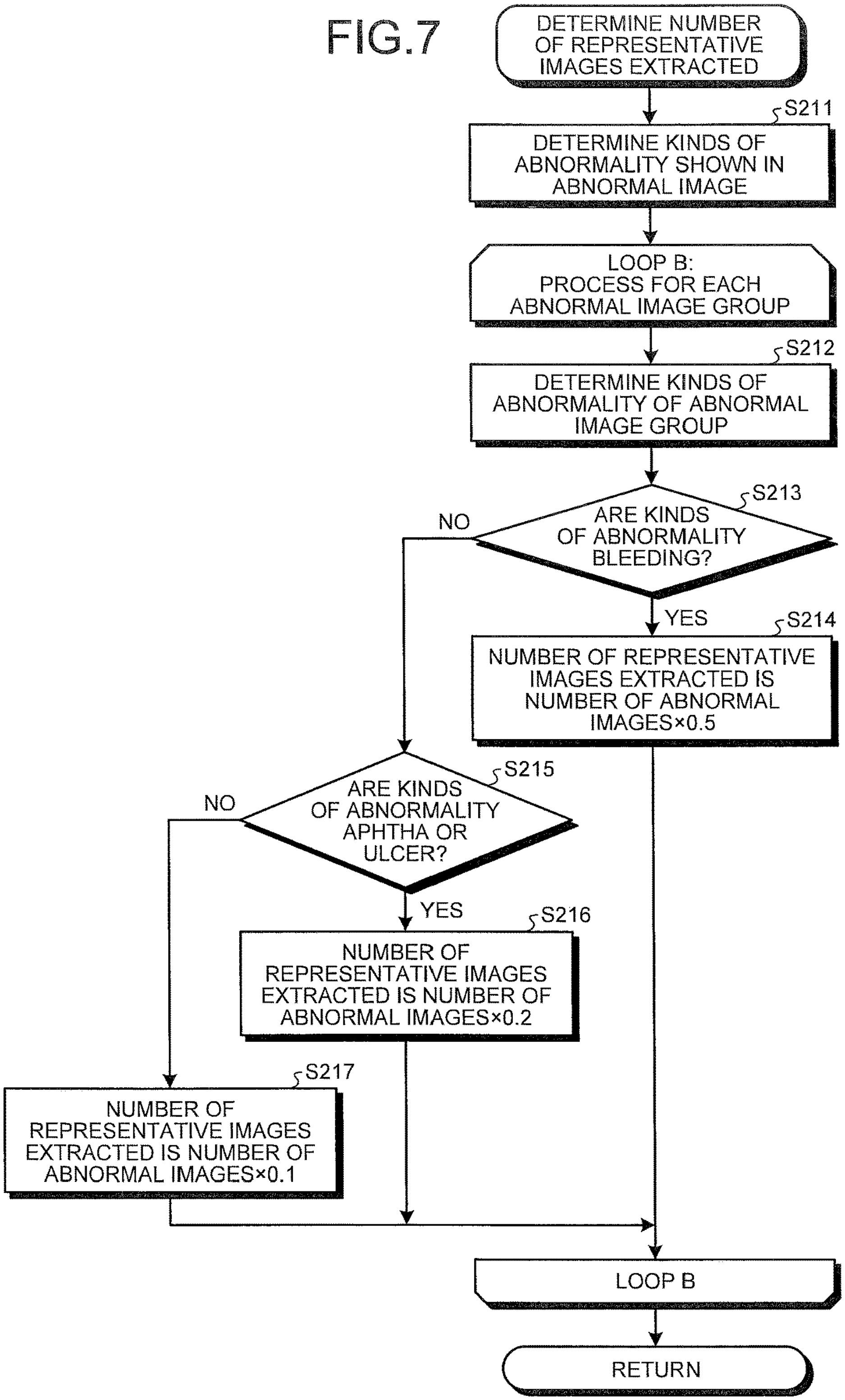
FIG. 7 is a flowchart illustrating a process of determining the number of representative images to be extracted, which is performed by a number-of-extracted-images determining unit according to modification 2-4 of the present invention.

FIG. 7 is a flowchart illustrating a process of determining the number of representative images to be extracted, which is performed by the number-of-extracted-images determining unit 210 according to modification 2-4. First, in step S211, the number-of-extracted-images determining unit 210 determines the kinds of abnormal region shown in each abnormal image extracted from a series of intraluminal images. For determination of the kinds of abnormal region, various known methods can be applied. For example, feature distribution of color features (e.g., values of R component, G component, and B component of a pixel value, values secondarily calculated by known conversion of the values of the color components (color difference calculated by YCbCr conversion, hue or saturation calculated by HSI conversion, color ratio such as G/R or B/G, or the like)), shape features (shape information such as histograms of oriented gradients (HOG), area, circumferential length, or Feret's diameter), or texture features (local binary pattern (LBP), simultaneous normal matrix, or the like) is previously calculated, based on various abnormal regions (bleeding, redness, or vascular abnormality, aphtha, ulcer or the like) shown in an intraluminal image. Then, based on the feature distribution, determination criteria are developed by a learning tool such as a support vector machine (SVM). Features calculated for the abnormal regions in the abnormal images are compared with the determination criteria, and the abnormal regions are classified into various abnormalities, that is, bleeding, redness, vascular abnormality, aphtha, and ulcer. In the following description, the bleeding is described as an abnormality having a relatively high degree of importance, the aphtha and the ulcer are described as abnormalities having an intermediate degree of importance, and the redness and the vascular abnormality are described as abnormalities having a relatively low degree of importance.

Next, the number-of-extracted-images determining unit 210 performs processing of a loop B for each abnormal image group.

In step S212, the number-of-extracted-images determining unit 210 determines the kinds of abnormal region of an abnormal image group to be processed. More specifically, based on a result of the classification of the abnormal regions in the abnormal image group, the most common (or major) kinds of abnormal region are determined as the kinds of abnormal region of the abnormal image group.

In the following step S213, the number-of-extracted-images determining unit 210 determines whether the kinds of abnormal region of the abnormal image group are bleeding. If the kinds of abnormal region are bleeding (step S213: Yes), the number-of-extracted-images determining unit 210 determines the number of representative images to be 0.5 times the number of abnormal images belonging to the abnormal image group (step S214).

In contrast, if the kinds of abnormal region are not bleeding (step S213: No), the number-of-extracted-images determining unit 210 then determines whether the kinds of abnormal region are the aphtha or ulcer (step S215). If the kinds of abnormal region are the aphtha or ulcer (step S215: Yes), the number-of-extracted-images determining unit 210 determines the number of representative images to be 0.2 times the number of abnormal images belonging to the abnormal image group (step S216).

Furthermore, if the kinds of abnormal region are not the aphtha or ulcer (step S215: No), the number-of-extracted-images determining unit 210 determines that the kinds of abnormal region of the abnormal image group are the redness or vascular abnormality, and determines the number of representative images to be 0.1 times the number of abnormal images belonging to the abnormal image group (step S217).

Note that, in step S214, S216, or S217, if an abnormal image group has the number of representative images to be extracted not more than one as a result of calculation of the number of representative images to be extracted, the number of representative images to be extracted is set to one.

After completion of the loop B for all abnormal image groups extracted from the series of intraluminal images, the processing by the number-of-extracted-images determining unit 210 returns to a main routine.

As described above, according to modification 2-4, the number of representative images to be extracted from each abnormal image group is determined according to the kinds of abnormal region, so that a larger number of representative images can be extracted from an abnormal image group including important abnormality such as bleeding. Accordingly, the user can prevent missing the abnormal region having a high degree of importance, to make accurate and efficient diagnosis.

Note that, in modification 2-4 described above, the kinds of abnormal regions detected from the intraluminal images are classified into the bleeding, aphtha, ulcer, redness, and vascular abnormality, but classification of abnormality is not limited to these. Furthermore, coefficients (0.5 times, 0.2 times, 0.1 times, or the like) set according to the kinds of abnormal images to determine the number of representative images to be extracted are also not limited to this description, and can be appropriately set according to the purpose of examination.

Modification 2-5

Next, modification 2-5 of the second embodiment of the present invention will be described.

In step S20 illustrated in FIG. 5, the number-of-extracted-images determining unit 210 may determine the number of representative images to be extracted, not only according to the types of organ or the kinds of abnormal region but also according to a combination thereof. For example, as in modification 2-4 described above, the number of representative images to be extracted is determined according to the kinds of abnormal region, for each abnormal image group, the number of representative images to be extracted is multiplied by a coefficient according to an organ of an abnormal image group, and the number of representative images to be extracted is finally obtained. For example, a coefficient according to an organ of an abnormal image group is preferably set to 1 for the organ to be examined, and set to 0.5 for an organ not to be examined.

Modification 2-6

Next, modification 2-6 of the second embodiment of the present invention will be described.

In step S20 illustrated in FIG. 5, the number-of-extracted-images determining unit 210 may adaptively determine the number of representative images to be extracted, based on the visibility of the abnormal image. Specifically, in order to prevent missing an abnormal region of an abnormal image group including an abnormal region having poor visibility, the number of representative images to be extracted is determined such that a larger number of representative images can be extracted. A method for determining the number of representative images to be extracted based on the brightness of the abnormal region will be described below, as an example of the degree of visibility of the abnormal image.

First, the number-of-extracted-images determining unit 210 calculates an average value (average luminance value) of G components of an abnormal region included in an abnormal image group to be processed. Then, the number of representative images to be extracted is determined such that a larger number of representative images can be extracted from an abnormal image group having an average luminance value less than a predetermined threshold. Specifically, when the abnormal image group has an average luminance value less than the predetermined threshold, the number of representative images to be extracted is determined to be 0.5 times the number of abnormal images belonging to the abnormal image group. In contrast, when the abnormal image group has an average luminance value not less than the predetermined threshold, the number of representative images to be extracted is determined to be 0.1 times the number of abnormal images belonging to the abnormal image group. Note that, if an abnormal image group has the number of representative images to be extracted not more than one as a result of calculation, the number of representative images to be extracted is set to one. Furthermore, coefficients (0.5 times, 0.1 times) for determining the number of representative images to be extracted may be appropriately changed.

Modification 2-7

Next, modification 2-7 of the second embodiment of the present invention will be described.

In step S20 illustrated in FIG. 5, the number-of-extracted-images determining unit 210 may determine the number of representative images to be extracted based on the contrast of the abnormal region, as another example of visibility of the abnormal image.

Specifically, first, the number-of-extracted-images determining unit 210 calculates an absolute value of a difference between an average value (average luminance value) of the G components in pixels constituting an abnormal region included in an abnormal image group to be processed, and an average value (average luminance value) of the G components in pixels constituting regions other than the abnormal region. Then, the number of representative images to be extracted is determined so that a larger number of representative images are extracted from an abnormal image group having an absolute value of a difference less than a predetermined threshold. Specifically, when the abnormal image group has an absolute value of a difference less than the predetermined threshold, the number of representative images to be extracted is determined to be 0.5 times the number of abnormal images belonging to the abnormal image group. In contrast, when an abnormal image group has an absolute value of a difference not less than the predetermined threshold, the number of representative images to be extracted is determined to be 0.1 times the number of abnormal images belonging to the abnormal image group. Note that, if an abnormal image group has the number of representative images to be extracted not more than one as a result of calculation, the number of representative images to be extracted is set to one. Furthermore, coefficients (0.5 times, 0.1 times) for determining the number of representative images to be extracted may be appropriately changed.

Modification 2-8

Next, modification 2-8 of the second embodiment of the present invention will be described.

In step S20 illustrated in FIG. 5, the number-of-extracted-images determining unit 210 may determine the number of representative images to be extracted based on the total area of the abnormal region in the abnormal image, as another example of visibility of the abnormal image.

Specifically, first, the number-of-extracted-images determining unit 210 calculates the total area of an abnormal region included in an abnormal image group to be processed. Then, the number of representative images to be extracted is determined such that a larger number of representative images can be extracted from an abnormal image group having a total area of the abnormal region less than a predetermined threshold. Specifically, when the abnormal image group has a total area of the abnormal region less than the predetermined threshold, the number of representative images to be extracted is determined to be 0.5 times the number of abnormal images belonging to the abnormal image group. In contrast, when the abnormal image group has a total area of the abnormal region not less than the predetermined threshold, the number of representative images to be extracted is determined to be 0.1 times the number of abnormal images belonging to the abnormal image group. Note that, if an abnormal image group has the number of representative images to be extracted not more than one as a result of calculation, the number of representative images to be extracted is set to one. Furthermore, coefficients (0.5 times, 0.1 times) for determining the number of representative images to be extracted may be appropriately changed.

Modification 2-9

Next, modification 2-9 of the second embodiment of the present invention will be described.

In step S20 illustrated in FIG. 5, the number-of-extracted-images determining unit 210 may determine the number of representative images to be extracted based on the total number of the abnormal regions in the abnormal image, as another example of visibility of the abnormal image.

Specifically, first, the number-of-extracted-images determining unit 210 calculates the total number of abnormal regions of an abnormal region included in an abnormal image group to be processed. Then, the number of representative images to be extracted is determined such that a larger number of representative images can be extracted from an abnormal image group having a total number of abnormal regions less than a predetermined threshold. Specifically, when the abnormal image group has a total number of abnormal regions less than the predetermined threshold, the number of representative images to be extracted is determined to be 0.5 times the number of abnormal images belonging to the abnormal image group. In contrast, when the abnormal image group has a total number of abnormal regions not less than the predetermined threshold, the number of representative images to be extracted is determined to be 0.1 times the number of abnormal images belonging to the abnormal image group. Note that, if an abnormal image group has the number of representative images to be extracted not more than one as a result of calculation, the number of representative images to be extracted is set to one. Furthermore, coefficients (0.5 times, 0.1 times) for determining the number of representative images to be extracted may be appropriately changed.

Third Embodiment

Next, a third embodiment of the present invention will be described.

Figure 8:
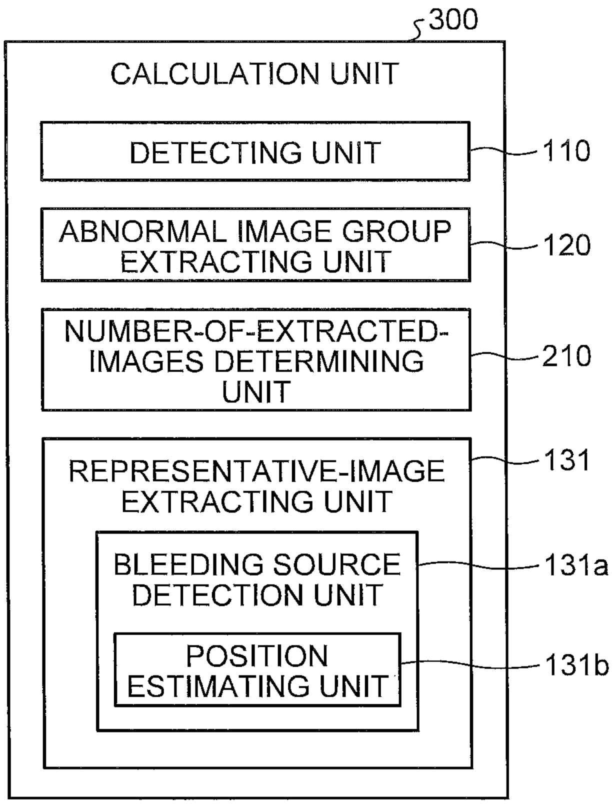
FIG. 8 is a block diagram illustrating a configuration of a calculation unit of an image processing apparatus according to a third embodiment of the present invention.

FIG. 8 is a block diagram illustrating a configuration of a calculation unit of an image processing apparatus according to the third embodiment of the present invention. As illustrated in FIG. 8, the image processing apparatus according to the third embodiment includes a calculation unit 300, instead of the calculation unit 100 illustrated in FIG. 1. Configurations and operations of units other than the calculation unit 300 are similar to those of the first embodiment.

The calculation unit 300 includes the detecting unit 110, the abnormal image group extracting unit 120, the number-of-extracted-images determining unit 210, and a representative-image extracting unit 131. Among these, operations of the detecting unit 110 and the abnormal image group extracting unit 120 are similar to those of the first embodiment. Furthermore, operation of the number-of-extracted-images determining unit 210 is similar to that of the second embodiment. Alternatively, the number-of-extracted-images determining unit 210 may be operated similarly to modifications 2-1 to 2-9.

The representative-image extracting unit 131 preferentially extracts, as the representative image, an abnormal image showing a bleeding source for the abnormal region having a high degree of importance, from each of the abnormal image groups each including identical abnormal regions. More specifically, the representative-image extracting unit 131 includes a bleeding source detection unit 131*a* for detecting a bleeding source from an abnormal image group showing a bleeding abnormal region. The bleeding source detection unit 131*a* includes a position estimating unit 131*b* for estimating a position, in a lumen, of an object (organ) shown in an abnormal image, that is, an imaging position in a lumen from which the abnormal image is captured.

Next, operation of the image processing apparatus according to the third embodiment will be described. Operation of the image processing apparatus according to the third embodiment is wholly similar to that in the second embodiment (see FIG. 5). In processing of extracting a representative image from each abnormal image group (step S13), when an abnormal region has bleeding, an abnormal image showing a particularly important bleeding source is extracted as the representative image. Note that, in the following description, the number of representative images to be extracted, determined for each abnormal image group in step S20, is defined as n.

Figure 9:
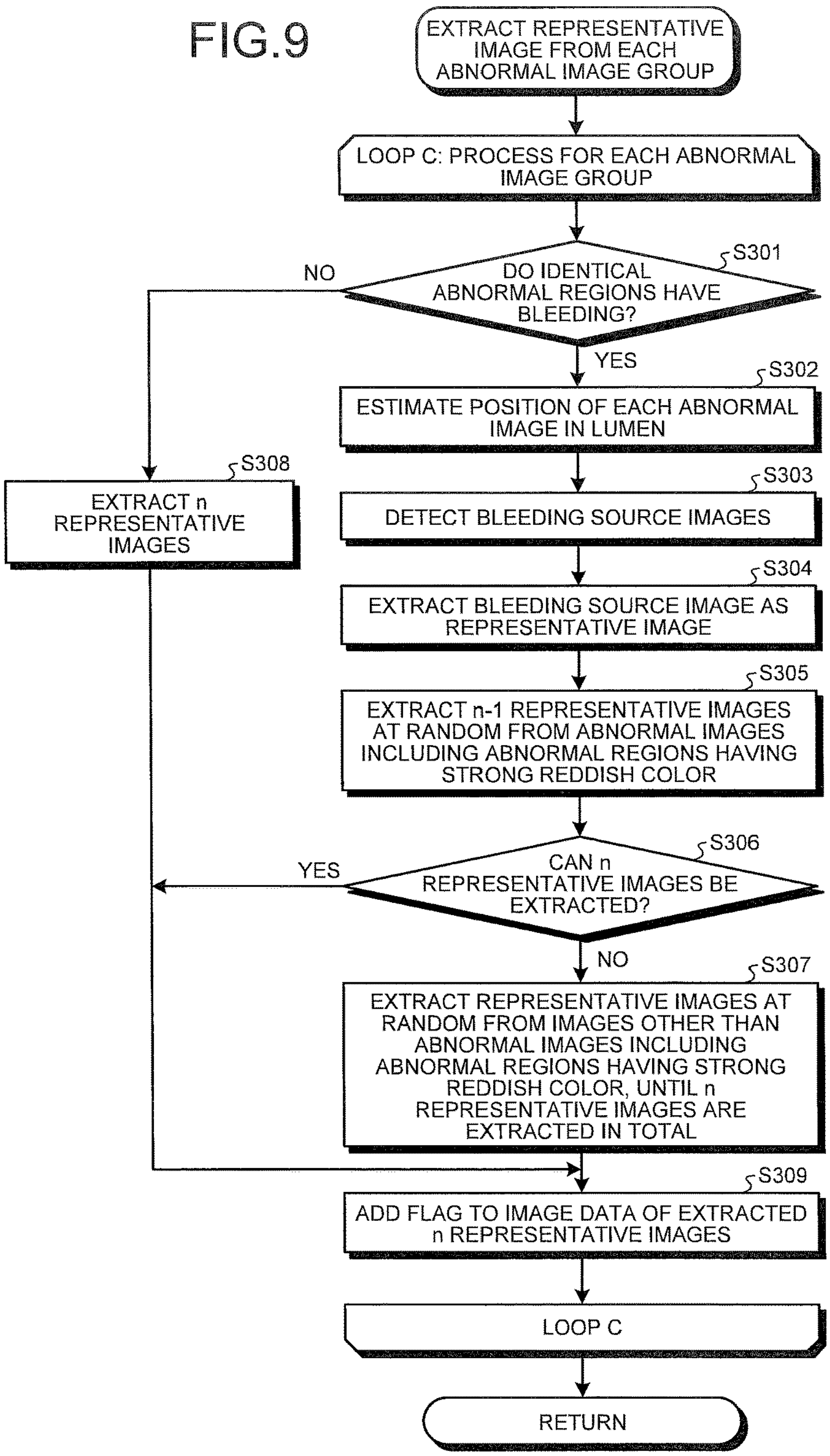
FIG. 9 is a flowchart illustrating a process of extracting a representative image, which is performed by a representative-image extracting unit illustrated in FIG. 8.

FIG. 9 is a flowchart illustrating a process of extracting a representative image, which is performed by the representative-image extracting unit 131. The representative-image extracting unit 131 performs processing of a loop C for each abnormal image group extracted in step S12.

First, in step S301, the representative-image extracting unit 131 determines whether identical abnormal regions in an abnormal image group to be processed have bleeding. Specifically, abnormal regions detected based on the specific reddish color in step S11 (see first embodiment) are determined as bleeding. Alternatively, similarly to modification 2-4, it may be determined whether the abnormal regions have bleeding, based on the color features, the shape features, and the texture features.

When the identical abnormal regions have bleeding (step S301: Yes), the position estimating unit 131*b* estimates an imaging position in a lumen from which each abnormal image belonging to the abnormal image group is captured, based on time-series positional information of each abnormal image, that is, arrangement sequence (imaging order) or imaging time in a series of intraluminal images (see FIG. 3) (step S302). For example, when a capsule endoscope used for imaging the series of intraluminal images has an average travel speed of v (e.g., 1 mm/second), and an imaging frame rate of F (e.g., 2 frames/second), the imaging position in an intraluminal image (abnormal image) $I_i$ can be estimated to be at a distance i·v/F (mm) from an imaging start position (e.g., in oral cavity) of the series of intraluminal images.

In the following step S303, the bleeding source detection unit 131*a* detects bleeding source images (abnormal image showing a bleeding source). Specifically, an abnormal image captured at an imaging position on the most upstream side in a lumen (i.e., the oldest time-series abnormal image) is detected, as the bleeding source image, from abnormal images including an abnormal region having a strong reddish color of the abnormal image group. Here, the abnormal region having a strong reddish color can be determined, for example, as a region having a color ratio G/R not more than a predetermined threshold. Note that, the threshold of the color ratio G/R used here is preferably set strictly (smaller value) relative to the determination criterion (color ratio G/R) used for detection of the abnormal region in step S11.

Generally, when bleeding is generated in a lumen, blood flows from an upstream side (oral cavity side) to a downstream side (anus side). Therefore, it can be considered that a bleeding source is shown in an abnormal image captured at an imaging position on the most upstream side of abnormal images including an abnormal region having a strong reddish color.

In the following step S304, the representative-image extracting unit 131 extracts, as the representative image, one of the bleeding source images detected in step S303.

In the following step S305, the representative-image extracting unit 131 extracts n−1 representative images at random from abnormal images including abnormal regions having a strong reddish color (excluding the bleeding source image) among the abnormal image group, where, n is the number of representative images to be extracted.

In the following step S306, the representative-image extracting unit 131 determines whether n representative images are extracted. If the abnormal image group has at least n abnormal images including the abnormal regions having a strong reddish color, a total of n representative images can be extracted from the at least n abnormal images. In this condition (step S306: Yes), the process proceeds to step S309.

In contrast, when the abnormal images including the abnormal regions having a strong reddish color is less than n, in the abnormal image group, n representative images cannot be extracted. In this condition (step S306: No), the representative-image extracting unit 131 extracts representative images from the remaining abnormal images not including the abnormal regions having a strong reddish color, until n representative images are extracted in total (step S307). Then, the process proceeds to step S309.

Furthermore, in step S301, if identical abnormal regions in an abnormal image group to be processed do not have the bleeding (step S301: No), the representative-image extracting unit 131 extracts n representative images from the abnormal image group, similarly to the first embodiment or modifications 1-1 to 1-8 of the first embodiment (step S308). Then, the process proceeds to step S309.

In step S309, the representative-image extracting unit 131 adds information (flag) indicating the representative image to image data of the extracted n representative images.

After completion of processing of the loop C for all abnormal image groups extracted in step S12 (see FIG. 5), the process returns to a main routine.

As described above, according to the third embodiment of the present invention, the bleeding source having a high degree of importance can be extracted as the representative image, based on the intensity of the reddish color of the abnormal region and the imaging position in a lumen from which each abnormal image is captured.

Fourth Embodiment

Next, a fourth embodiment of the present invention will be described.

Figure 10:
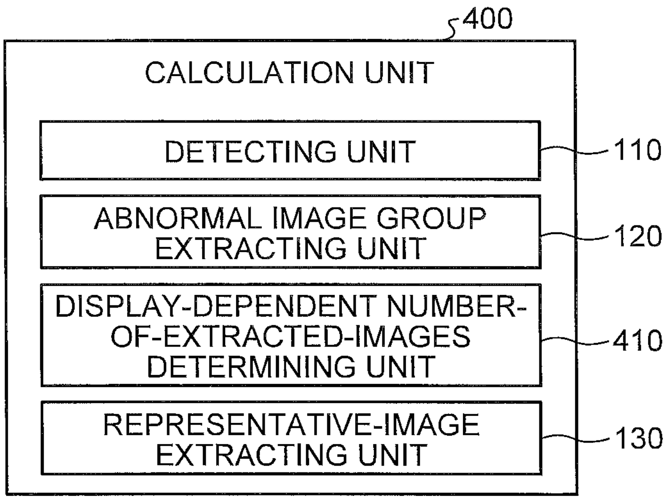
FIG. 10 is a block diagram illustrating a configuration of a calculation unit of an image processing apparatus according to a fourth embodiment of the present invention.

FIG. 10 is a block diagram illustrating a configuration of a calculation unit of an image processing apparatus according to the fourth embodiment of the present invention. As illustrated in FIG. 10, the image processing apparatus according to the fourth embodiment includes a calculation unit 400 illustrated in FIG. 10, instead of the calculation unit 100 illustrated in FIG. 1. Configurations and operations of units other than the calculation unit 400 are similar to those of the first embodiment.

The calculation unit 400 includes the detecting unit 110, the abnormal image group extracting unit 120, a display-dependent number-of-extracted-images determining unit 410, and the representative-image extracting unit 130. Among these, operations of the detecting unit 110, the abnormal image group extracting unit 120, and the representative-image extracting unit 130 are similar to those of the first embodiment.

The display-dependent number-of-extracted-images determining unit 410 adaptively determines the number of representative images to be extracted from each abnormal image group, according to a display method of representative images (displaying moving image or displaying still image).

Figure 11:
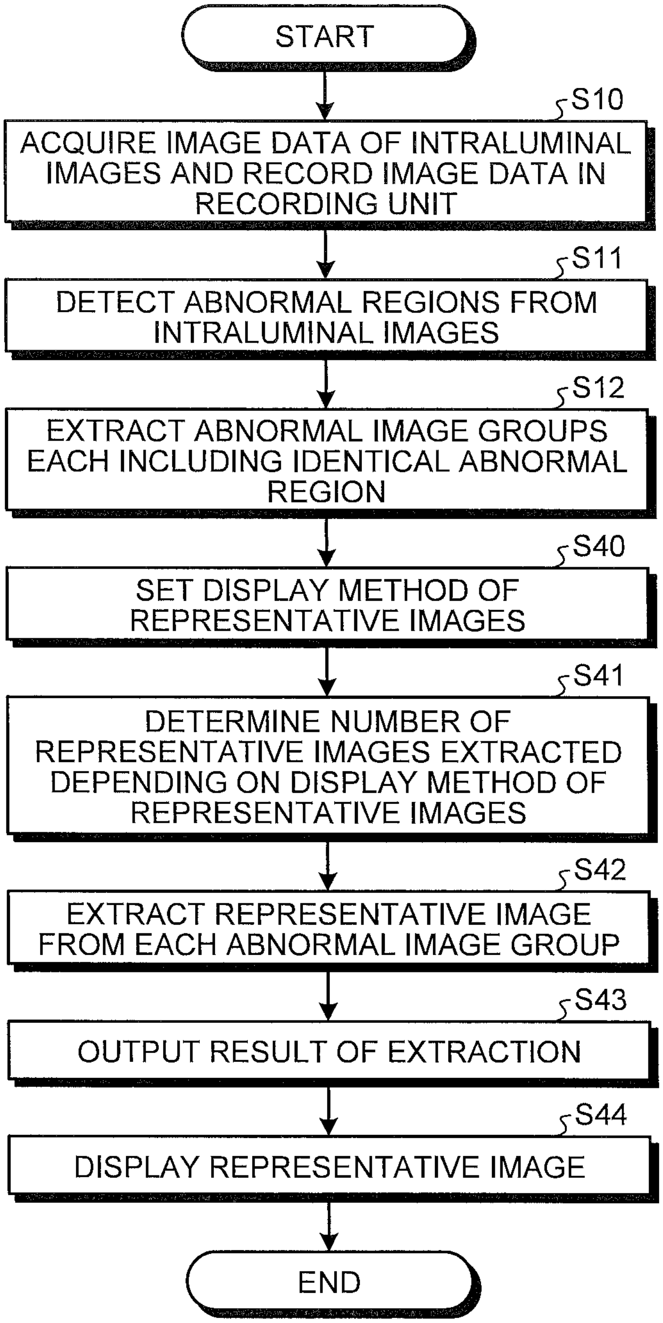
FIG. 11 is a flowchart illustrating operation of the image processing apparatus according to the fourth embodiment of the present invention.

Next, operation of the image processing apparatus according to the fourth embodiment will be described. FIG. 11 is a flowchart illustrating operation of the image processing apparatus according to the fourth embodiment of the present invention. Note that, steps S10 to S12 illustrated in FIG. 11 are similar to those of the first embodiment (see FIG. 2).

In step S40 subsequent to step S12, when a signal for instructing a display method of representative images is input from the input unit 30 to the control unit 10, according to user' operation on the input unit 30, the control unit 10 sets the display method of representative images according to the signal.

In the following step S41, the display-dependent number-of-extracted-images determining unit 410 adaptively determines the number of representative images to be extracted from each abnormal image group, depending on the display method set in step S41. Here, when a moving image of the representative images are displayed, missing the abnormal region tends to occur, compared with displaying a still image. Therefore, in order to prevent missing the abnormal region, upon displaying the moving image, the number of representative images to be extracted is determined such that a larger number of representative images can be extracted.

Specifically, when the moving image is displayed, the display-dependent number-of-extracted-images determining unit 410 determines the number of representative images to be extracted, to be 0.5 times the number of abnormal images belonging to the abnormal image group. In contrast, when the still image is displayed, the number of representative images to be extracted is determined to be 0.1 times the number of abnormal images belonging to the abnormal image group. Note that, if an abnormal image group has the number of representative images to be extracted not more than one as a result of calculation, the number of representative images to be extracted is set to one. Furthermore, coefficients (0.5 times, 0.1 times) for determining the number of representative images to be extracted may be appropriately changed.

In the following step S42, the representative-image extracting unit 130 extracts, as the representative image, abnormal images having a high degree of importance of the abnormal region, or abnormal images having good visibility of the abnormal region, from each of the abnormal image groups extracted in step S12, where the number of abnormal images extracted is determined in step S41. The representative image extraction method is similar to those in the first embodiment, modifications 1-1 to 1-8, or the third embodiment.

In the following step S43, the calculation unit 400 outputs information indicating the representative image extracted from each abnormal image group in step S42. Accordingly, the recording unit 50 adds information (flag) indicating the representative image to image data of the intraluminal image extracted as the representative image.

In the following step S44, the display unit 40 displays the representative image extracted in step S43, under the instruction of the control unit 10. Specifically, the control unit 10 reads the image data to which the flag is added in step S43 from the recording unit 50, outputs the image data to the display unit 40, and displays the representative image on the display unit 40, based on the image data, according to the display method set in step S40.

As described above, according to the fourth embodiment of the present invention, since the number of representative images to be extracted from each abnormal image group is adaptively determined depending on the display method of representative images, the number of representative images to be extracted is increased for displaying the moving image to prevent missing the abnormal region, and reduced for displaying the still image to perform efficient image observation.

Modification 4-1

Next, modification 4-1 of the fourth embodiment of the present invention will be described.

In the above description, the process of determining the number of representative images to be extracted and the process of extracting a representative image are performed whenever image display is performed, but the processes may be performed beforehand. That is, an image data set of representative images extracted for displaying the moving image, and an image data set of a representative image extracted for displaying the still image are prepared in respective formats, and recorded in the recording unit 50, for a series of intraluminal images. When a signal for specifying a display method of representative images is input from the input unit 30 to the control unit 10, for image display, according to user's operation on the input unit 30, the control unit 10 reads an image data set from the recording unit 50 according to the specified display method, for display on the display unit 40.

Modification 4-2

Next, modification 4-2 of the fourth embodiment of the present invention will be described.

The process of determining the number of representative images to be extracted in the fourth embodiment may be combined with another process of determining the number of representative images to be extracted. Specifically, as described in the second embodiment or modifications 2-1 to 2-9, the number of representative images to be extracted is determined for each abnormal image group, based on the degree of importance or visibility of the abnormal region, and further, the determined number of representative images to be extracted is multiplied by a coefficient according to a display method of representative images, and finally, the number of representative images to be extracted is obtained. For example, a coefficient according to the display method of representative images is preferably set to 1 for displaying the moving image, and set to 0.5 for displaying the still image.

The image processing apparatus according to the first to fourth embodiments and the modifications of the first to fourth embodiments described above can be achieved by executing image processing programs recorded in a recording medium, on a computer system such as a personal computer or workstation. Furthermore, such a computer system may be used by being connected to another computer system or a device such as a server, through a public network such as a local area network (LAN), a wide area network (WAN), or a public network such as the Internet. In this configuration, the image processing apparatus according to the first to fourth embodiments and the modifications of the first to fourth embodiments may acquire image data of the intraluminal images through these networks, may output a result of image processing to various output devices (viewer, printer, and the like) connected through these networks, or may store a result of image processing in a storage device (recording medium, reader thereof, and the like) connected through these networks.

According to some embodiments, image-of-interest groups each including an identical region of interest are extracted from a group of a series of images acquired by imaging a lumen of a living body in chronological order, and a representative image is extracted from each of the image-of-interest groups based on at least one of a correlation of each region of interest with an object to be detected, and visibility of each region of interest. Therefore, it is possible to preferentially extract a beneficial image for diagnosis as a representative image.

Note that, the present invention is not limited to the first to fourth embodiments and modifications of the first to fourth embodiments, and invention may be variously made by appropriately combining the elements disclosed in the embodiments or modifications. For example, the present invention may be made by removing several elements from all the elements described in the embodiments or modifications, or by appropriately combining the elements described in different embodiments or modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:

a processor comprising hardware, wherein the processor is configured to:

detect images of interest including regions of interest that are estimated as an object to be detected, from a series of images acquired by sequentially imaging a lumen of a living body;

extract a group of images of interest including an identical region of interest, from the images of interest detected;

detect a bleeding source shown in the images of interest belonging to the group of images of interest; and extract one or more predetermined number of representative images from the group of images of interest, wherein the one or more predetermined number of representative images comprises images of interest showing the bleeding source detected, wherein each of the one or more predetermined number of representative images is an image of interest that is higher in at least one of correlation of the regions of interest with the object to be detected and visibility of the regions of interest than a remaining one or more remaining images of interest in the group of images of interest, and wherein a region of interest having a higher likelihood of being the bleeding source is considered to have a higher correlation with the object to be detected for the purpose of extracting the one or more predetermined number of representative images from the group of images of interest.

2. The image processing apparatus according to claim 1, wherein the processor is configured to detect the images of interest by threshold processing for features of each image included in the series of images.

3. The image processing apparatus according to claim 2, wherein the processor is configured to detect an unnecessary region having no correlation with the object to be detected, and wherein a region of interest in an image of interest having a smaller unnecessary region is considered to be higher in visibility for the purpose of extracting the one or more predetermined number of representative images from the group of images of interest.

4. The image processing apparatus according to claim 3, wherein the unnecessary region is a region showing at least one of noise, bubble, and residue.

5. The image processing apparatus according to claim 2, wherein the processor is configured to calculate intensity of reddish color of the regions of interest in the images of interest, and wherein a region of interest having a higher intensity of the reddish color is considered to have a higher correlation with the object to be detected for the purpose of extracting the one or more predetermined number of representative images from the group of images of interest.

6. The image processing apparatus according to claim 2, wherein the processor is configured to calculate intensity of white color of the regions of interest in the images of interest, and wherein a region of interest having a higher intensity of the white color is considered to have a higher correlation with the object to be detected for the purpose of extracting the one or more predetermined number of representative images from the group of images of interest.

7. The image processing apparatus according to claim 2, wherein the processor is configured to calculate brightness of the regions of interest in the images of interest, and wherein a region of interest having a higher brightness is considered to be higher in visibility for the purpose of extracting the one or more predetermined number of representative images from the group of images of interest.

8. The image processing apparatus according to claim 2, wherein the processor is configured to calculate contrast of the regions of interest in the images of interest, and wherein a region of interest having a higher contrast is considered to be higher in visibility for the purpose of extracting the one or more predetermined number of representative images from the group of images of interest.

9. The image processing apparatus according to claim 2, wherein the processor is configured to calculate one of areas of the regions of interest in the images of interest, and number of the regions of interest in the images of interest, and wherein a region of interest having one of a larger area or a larger number of regions of interest is considered to be higher in visibility for the purpose of extracting the one or more predetermined number of representative images from the group of images of interest.

10. The image processing apparatus according to claim 2, wherein the processor is configured to calculate, for each image of interest in the group of images of interest, a shortest distance between the identical region of interest included in the each image of interest in the group of images of interest and one of sides of the each image of interest in the group of images of interest, and wherein an image of interest in the group of images of interest having a longer of the shortest distance is considered to be higher in visibility for the purpose of extracting the one or more predetermined number of representative images from the group of images of interest.

11. The image processing apparatus according to claim 1, wherein the processor is configured to:

estimate a position of a subject in the lumen shown in the images of interest belonging to the group of images of interest; and detect the bleeding source based on the position.

12. The image processing apparatus according to claim 1, wherein the processor is configured to determine the number of representative images to be extracted, based on at least one of the correlation and the visibility in the group of images of interest extracted.

13. The image processing apparatus according to claim 12, wherein the processor is configured to:

determine whether an organ shown in images of interest belonging to the group of images of interest is the object to be examined; and adaptively determine the number of representative images to be extracted, based on a result of the determination.

14. The image processing apparatus according to claim 12, wherein the processor is configured to:

classify kinds of the regions of interest included in the group of images of interest; and adaptively determine the number of representative images to be extracted, based on the kinds of the regions of interest.

15. The image processing apparatus according to claim 12, wherein the processor is configured to:

calculate brightness of the regions of interest included in the group of images of interest; and adaptively determine the number of representative images to be extracted, based on the brightness.

16. The image processing apparatus according to claim 12, wherein the processor is configured to:

calculate contrast of the regions of interest included in the group of images of interest; and adaptively determine the number of representative images to be extracted, based on the contrast.

17. The image processing apparatus according to claim 12, wherein the processor is configured to:

calculate one of areas of the regions of interest included in the group of images of interest, and number of the regions of interest included in the group of images of interest; and adaptively determine the number of representative images to be extracted, based on one of the areas and the number of the regions of interest.

18. The image processing apparatus according to claim 1, wherein the processor is configured to adaptively determine the number of representative images to be extracted, depending on a display method of the representative images.

19. An image processing method comprising:

detecting images of interest including regions of interest that are estimated as an object to be detected, from a series of images acquired by sequentially imaging a lumen of a living body;

extracting a group of images of interest including an identical region of interest, from the detected images of interest;

detecting a bleeding source shown in the images of interest belonging to the group of images of interest; and extracting one or more predetermined number of representative images from the group of images of interest, wherein the one or more predetermined number of representative images comprises images of interest showing the bleeding source detected, wherein each of the one or more predetermined number of representative images is an image of interest that is higher in at least one of correlation of the regions of interest with the object to be detected and visibility of the regions of interest, than a remaining one or more remaining images of interest in the group of images of interest; and wherein a region of interest having a higher likelihood of being the bleeding source is considered to have a higher correlation with the object to be detected for the purpose of extracting the one or more predetermined number of representative images from the group of images of interest.

20. An image processing apparatus comprising:

a processor comprising hardware, wherein the processor is configured to:

detect images of interest including regions of interest that are estimated as an object to be detected, from a series of images acquired by sequentially imaging a lumen of a living body;

extract a group of images of interest including an identical region of interest, from the images of interest detected;

calculate, for each image of interest in the group of images of interest, a shortest distance between the region of interest included in the each image of interest in the group of images of interest and one of sides of the each image of interest in the group of images of interest; and extract one or more representative images from the group of images of interest, based on visibility of the regions of interest, wherein an image of interest in the group of images of interest having a longer of the shortest distance is considered to be higher in visibility for the purpose of extracting the one or more predetermined number of representative images from the group of images of interest.

21. An image processing apparatus comprising:

a processor comprising hardware, wherein the processor is configured to:

detect images of interest including regions of interest that are estimated as an object to be detected, from a series of images acquired by sequentially imaging a lumen of a living body;

extract a group of images of interest including an identical region of interest, from the images of interest detected;

determine whether an organ shown in images of interest belonging to the group of images of interest is the object to be examined;

adaptively determine a number of representative images to be extracted, based on a result of determination; and extract the determined number of representative images from the group of images of interest, based on at least one of correlation of the regions of interest with the object to be detected and visibility of the regions of interest.

* * * * *